United States Patent
Wilson

[11] Patent Number: 5,695,526
[45] Date of Patent: *Dec. 9, 1997

[54] ONE-PIECE MECHANICALLY DIFFERENTIATED PROSTHETIC FOOT AND ASSOCIATED ANKLE JOINT WITH SYME MODIFICATION

[76] Inventor: Michael T. Wilson, 3131 Villa La., Missouri City, Tex. 77459

[*] Notice: The term of this patent shall not extend beyond the expiration date of Pat. No. 5,443,527.

[21] Appl. No.: 381,073

[22] Filed: Jan. 31, 1995

Related U.S. Application Data

[63] Continuation-in-part of Ser. No. 40,905, Mar. 31, 1995, Pat. No. 5,443,527, and a continuation-in-part of Ser. No. 134,384, Oct. 12, 1993, Pat. No. 5,482,513.

[51] Int. Cl.⁶ .................................................... A61F 2/66
[52] U.S. Cl. .................................................... 623/49; 623/53
[58] Field of Search .......................... 623/55, 53, 47–52, 623/54, 56

[56] References Cited

U.S. PATENT DOCUMENTS

| | | |
|---|---|---|
| 409,311 | 8/1889 | Snyder . |
| 419,019 | 1/1890 | Kolbe . |
| 766,686 | 8/1904 | Gault ............................. 623/55 X |
| 1,071,230 | 8/1913 | Hanger . |
| 1,294,632 | 2/1919 | Dickson . |
| 2,450,728 | 10/1948 | Havens . |
| 2,594,752 | 4/1952 | Fahlstrom . |
| 2,605,475 | 8/1952 | Burger et al. ................... 623/49 |
| 2,620,485 | 12/1952 | Greissinger . |
| 2,731,645 | 1/1956 | Woodall . |
| 2,745,108 | 5/1956 | Withers .......................... 623/55 |
| 3,196,463 | 7/1965 | Farneth . |
| 3,480,972 | 12/1969 | Prahl . |
| 3,940,804 | 3/1976 | Benton et al. . |
| 3,982,278 | 9/1976 | May . |
| 4,328,594 | 5/1982 | Campbell et al. . |
| 4,446,580 | 5/1984 | Furuya et al. . |
| 4,461,045 | 7/1984 | Shorter et al. . |
| 4,463,459 | 8/1984 | Shorter et al. . |
| 4,547,913 | 10/1985 | Phillips ......................... 623/27 |
| 4,645,509 | 2/1987 | Poggi et al. .................... 623/55 |
| 4,721,510 | 1/1988 | Cooper et al. .................. 623/55 |
| 4,764,172 | 8/1988 | McCoy ........................... 623/49 |
| 4,822,363 | 4/1989 | Phillips ......................... 623/27 |
| 4,889,458 | 12/1989 | Taylor ........................... 411/383 |
| 4,892,554 | 1/1990 | Robinson ....................... 623/55 |
| 4,969,911 | 11/1990 | Greene .......................... 623/38 |
| 5,030,239 | 7/1991 | Copes ............................ 623/52 |
| 5,112,356 | 5/1992 | Harris et al. ................... 623/49 |
| 5,158,570 | 10/1992 | Schey et al. ................... 623/52 |
| 5,219,364 | 6/1993 | Lloyd ............................ 623/33 |
| 5,258,038 | 11/1993 | Robinson et al. ............... 623/49 |
| 5,376,140 | 12/1994 | Ryan ............................. 623/55 |
| 5,443,527 | 8/1995 | Wilson ........................... 623/49 |

FOREIGN PATENT DOCUMENTS

| | | | |
|---|---|---|---|
| 0196553 | 3/1958 | Austria ........................... 623/53 |
| 224373 | 6/1947 | European Pat. Off. . |
| 0481770 | 10/1916 | France ............................ 623/53 |

(List continued on next page.)

OTHER PUBLICATIONS

Flex–Foot, Inc. flyers entitled, "Something Revolutionary Is In The Air," Adjust the foot, not the lifestyle, Engineered For The Long Run, Simply Precise, Engineered Flexibility, Designed For A Growing Market, Amputee Profile (Mary Jane Gardner), Amputee Profile (Dan Broome), and Flex–Foot, Inc. Newsletter, Issue No. 4, 1992.

(List continued on next page.)

*Primary Examiner*—David H. Willse
*Attorney, Agent, or Firm*—Conley, Rose & Tayon, P.C.

[57] ABSTRACT

A lightweight foot prosthesis is claimed, being formed from a single piece of material and having a heel, a raised instep having a groove adjacent its lower surface and forward and rear contact surfaces, the contact surfaces defining a saddle-shaped surface therebetween, and a substantially flat toe.

18 Claims, 11 Drawing Sheets

FOREIGN PATENT DOCUMENTS

| | | | |
|---|---|---|---|
| 504342 | 6/1920 | France . | |
| 1233031 | 10/1960 | France | 623/50 |
| 2640499 | 6/1990 | France | 623/53 |
| 814025 | 9/1951 | Germany . | |
| 2241971 | 3/1974 | Germany | 623/55 |
| 9104823 | 7/1991 | Germany . | |
| 1424831 | 9/1988 | U.S.S.R. | 623/55 |
| 1747062 | 7/1992 | U.S.S.R. | 623/47 |
| 0227290 | 1/1925 | United Kingdom | 623/53 |
| 0621576 | 4/1949 | United Kingdom | 623/55 |
| 731223 | 6/1955 | United Kingdom . | |
| 2070439 | 9/1981 | United Kingdom | 623/47 |
| 2092451 | 8/1982 | United Kingdom | 623/53 |
| 8800815 | 2/1988 | WIPO | 623/55 |
| 8806431 | 7/1988 | WIPO . | |
| 8806431 | 9/1988 | WIPO | 623/53 |

OTHER PUBLICATIONS

Otto Bock flyer, "1M1—Otto Bock Multiaxial Foot".
Campbell–Childs, Inc. brochure and flyer entitled, "The All New 'Sportsman' S.A.F.E. II".
Devcon instruction sheet on "Flexane® Urethane".
Boston Gear catalogue, Self–Aligned Bearings, p. D68.
Hosmer, The Quantum Foot—Brochure.
Campbell–Childs, Inc. Stationary Attachment Flexible Endoskeleton II Mailer, Jul. 1989.
Campbell–Childs, Inc.—S.A.F.E. Prosthetic Foot Catalog.
United States Manufacturing Company—Multiplex Brochure.
The Ohio Willow Wood Co., Step into the Future with the Carbon Copy II Energy Storing Foot.
Footnotes (Flex–Foot)—Mailer, Mar. 1989.
Flex–Foot, Inc.—Price List.

ONE-PIECE MECHANICALLY DIFFERENTIATED PROSTHETIC FOOT AND ASSOCIATED ANKLE JOINT WITH SYME MODIFICATION

This application is a continuation-in-part of application Ser. No. 08/040,905, filed on Mar. 31, 1993, now U.S. Pat. No. 5,443,527, and application Ser. No. 08/134,384, filed on Oct. 12, 1993, now U.S. Pat. No. 5,482,513, both of which are hereby incorporated by reference as if fully set forth herein.

1. Technical Field of the Invention

The present invention relates to the foot section of an artificial leg and more particularly to a prosthetic foot specifically designed for geriatric users and others who require less massive prostheses. Still more particularly, the present invention relates to construction of a prosthetic foot that is particularly adapted to be used by amputees who have undergone ankle disarticulation.

2. Background of the Invention

Prosthetic feet are well known in the art, and several such feet have been designed to accomplish one or more objectives.

A useful prosthesis will simulate the operation and motion of an anatomical foot to a desired degree. An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement up and down of the ball of the foot with respect to the heel that occurs during a normal forward step. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

Known foot prostheses include commercial feet that are capable of all three types of rotation. Typically, however, the joints capable of such complicated motion require bulky moving parts and are generally far too heavy for geriatric or very young patients, or other patients who suffer some degree of muscular weakness. Furthermore, some patients may not require high degree of flexibility, and may even desire the increased stability associated with a prosthesis that is capable of rotation about a single axis. Such a prosthesis would allow dorsiflexion and planiflexion, but not inversion, eversion, or transverse rotation. This would permit a near-normal step during forward motion, and would reduce the likelihood that the wearer might lose his or her balance as a result of uncontrolled or unintended rotation about one of the other axes.

In addition, it is desirable for a foot prosthesis to be capable of absorbing, storing, and releasing energy, so that the prosthesis returns itself to a relaxed, unflexed position when the moving force is removed. Prostheses that are designed for use during athletic activities, such as running or playing basketball, are particularly efficient at energy storage and return, providing a springy step. Such energy storage is typically accomplished by the inclusion of coil springs or other reciprocating means which absorb energy on flexure and release it efficiently upon removal of the applied force. The energy-storing components that are typically used for efficient energy return can contribute significantly to the weight of the prosthesis.

In contrast, older, less mobile wearers neither need nor want a high degree of return of stored energy. Instead, it is preferable for the prostheses worn by these wearers to absorb and dissipate a portion of the energy of each flexion while retaining sufficient energy to return the prosthesis to its unflexed position. This provides a more stable, cushioned step, and reduces the shock experienced by both the wearer and the prosthesis at each step.

Finally, it is necessary that a foot prosthesis be strong enough to support its wearer and durable enough to withstand the stresses of repeated stepping motions over long periods of time. Conventional prostheses tend to be designed for maximize strength, at the cost of added bulk and weight, making them unsuitable for geriatric or very young wearers, who do not subject their prostheses to the same loads as the average wearer.

Hence it is desired to provide a flexible, durable prosthesis that provides a slightly damped step and requires a minimal mass.

In addition to amputations involving removal of the foot, ankle and lower leg, in which the prosthesis must include replacements for these parts, a common surgical procedure for the amputation of feet is ankle disarticulation, which leaves lower leg intact but leaves the amputee with an immobile nub in place of the ankle. Amputees who have undergone ankle disarticulation have very little clearance between the floor and this ankle nub. The foot prostheses known in the art either will not fit into this clearance, or do not provide an articulated prosthetic ankle joint.

SUMMARY OF THE INVENTION

The present invention comprises a foot prosthesis having a light-weight foot portion and an attached light-weight ankle portion capable of a desired degree of rotation around one or more axes. As used herein, the words "prosthesis" or "foot prosthesis" will refer to both the foot portion of a prosthetic foot and the ankle joint attached thereto.

Simplified construction of the foot and joint mechanisms enables the present invention to be at least about 50% lighter than typical foot prostheses. The foot portion of the prosthesis includes an integral instep and sole constructed of light weight polymeric material and is designed to provide support and flexure without added weight. The ankle portion of the prosthesis includes a transverse-mounted joint that provides desired flexibility and stability without excess mass. The present joint can be adapted to allow all three types of rotation, or to allow dorsiflexion and planiflexion and avoid flexibility with respect to other types of rotation.

While one embodiment of the present invention includes a connector for affixing the present foot prosthesis to the end of a prosthetic leg, the present invention further comprises an embodiment adapted for connection to the terminal end of a human leg from which the foot has been amputated. The present joint is easily attached to the lower leg of such amputees and allows them the mobility of an ankle-jointed foot. Further according to this embodiment, the foot portion of the prosthesis is modified to allow the joint to be positioned very close to the plantar surface of the foot, allowing it to be work by ankle disarticulation amputees and resulting in improved safety and comfort for the wearer.

Other objects and advantages of the present invention will appear from the following description.

BRIEF DESCRIPTION OF THE DRAWINGS

For a detailed description of a preferred embodiment of the invention, reference will now be made to the accompanying drawings wherein.

DETAILED DESCRIPTION OF THE INVENTION

The present invention comprises a lightweight foot prosthesis, an ankle joint affixed to said foot, such that the foot is capable of motion around at least one axis, and means for limiting rotation of said ankle joint and means for connecting said ankle joint to a leg. The foot prosthesis includes a naturally-shaped foot having a dorsal surface and a plantar surface and comprising a heel, a toe and a raised instep. Both the foot prosthesis and ankle joint have multiple embodiments that include adaptations for conventional amputees and for ankle disarticulation patients.

Referring initially to FIGS. 1–4, a first embodiment of the present prosthetic foot 10 includes a foot prosthesis 20, an attached ankle joint 30, and a connector 40. A prosthetic shin, or leg, which would normally be attached to connector 40 via a conventional connection is shown in phantom extending upward from connector 40 in FIG. 1. For purposes of discussion, the x, y, and z axes, about which an anatomical foot can rotate, are shown and have been assigned as follows. The x axis is perpendicular to both the leg and foot, passing through the sides of the ankle. The y axis is perpendicular to the leg and parallel to the foot, and the z axis is parallel to the leg.

Foot Prosthesis

Figure 1:
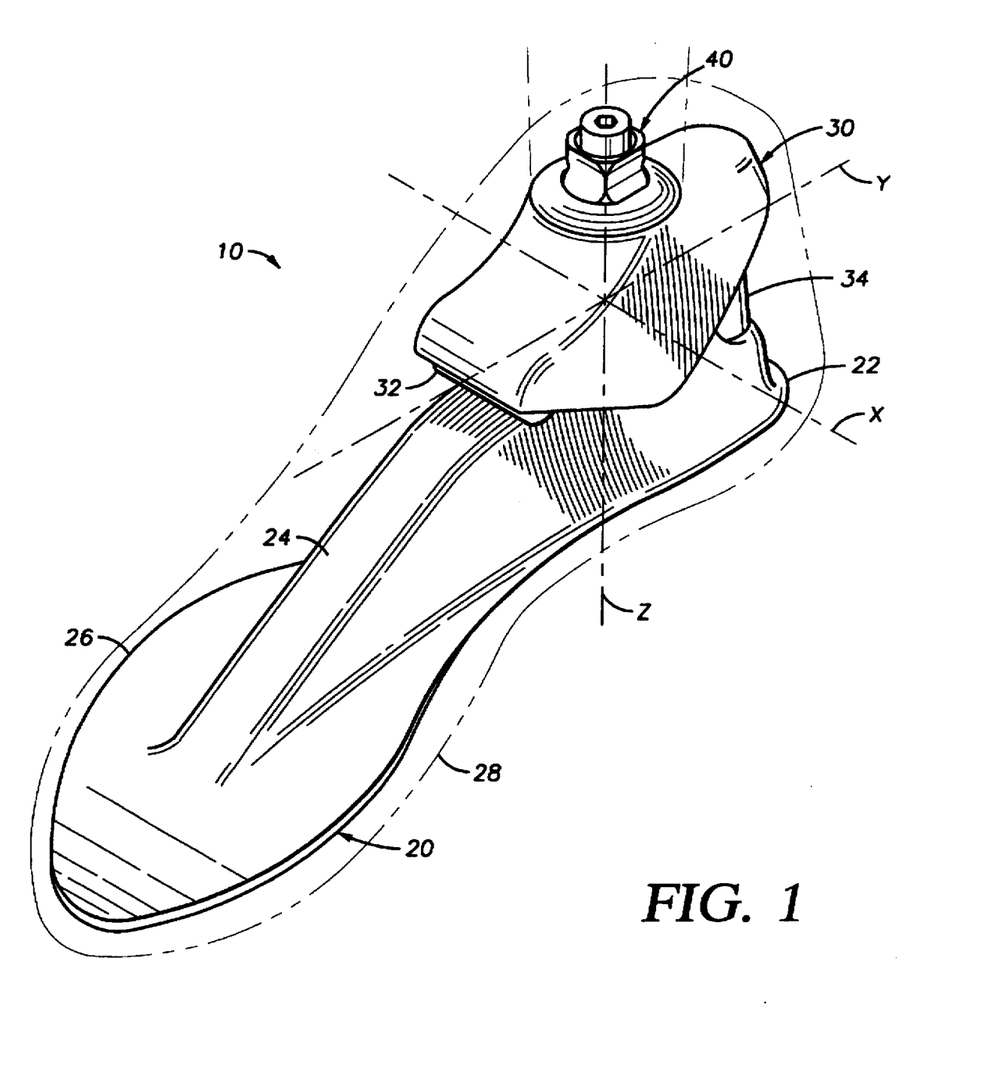
FIG. 1 is a perspective view of a prosthetic foot according to the present invention constructed with a first foot embodiment and a first ankle joint embodiment, wherein the surrounding cosmesis is shown in phantom.
Figure 2:
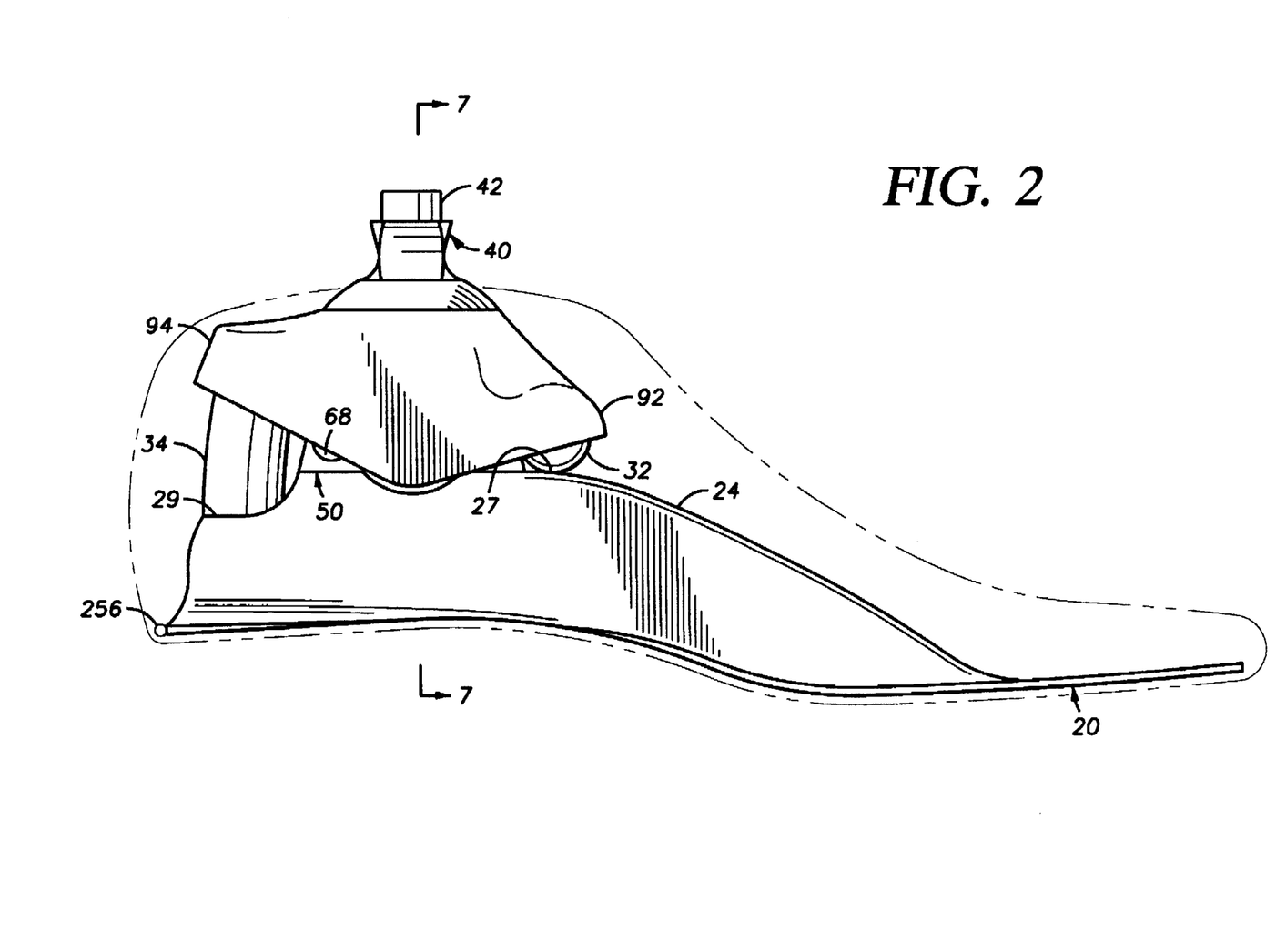
FIG. 2 is a side elevation of the prosthetic foot of FIG. 1.
Figure 3:
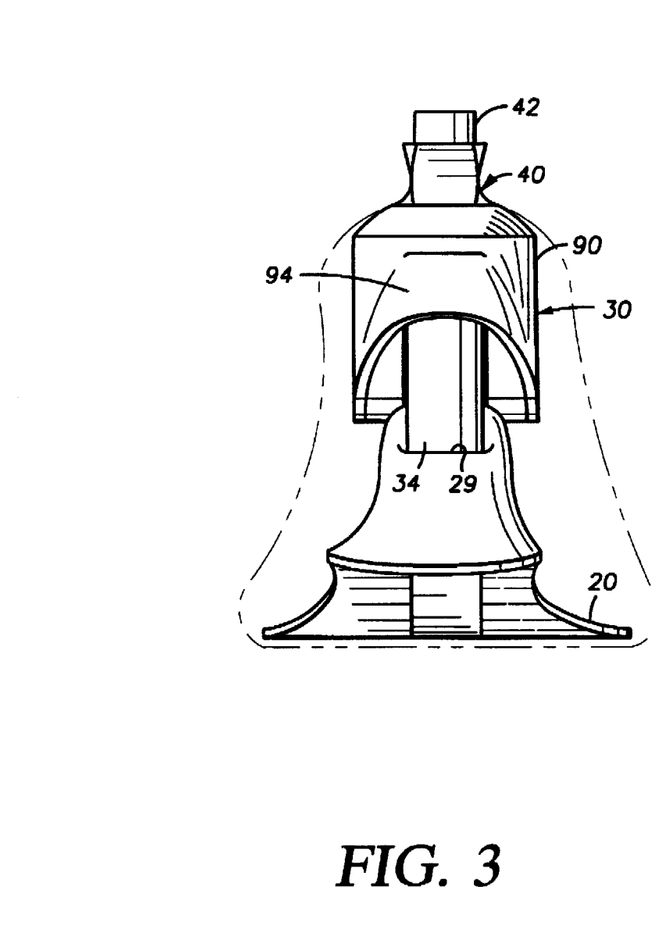
FIG. 3 is a rear elevation of the prosthetic foot of FIG. 1.

Referring particularly to FIG. 1, a first embodiment of foot prosthesis 20 comprises a heel 22, a raised instep 24, and a substantially flat toe portion 26. Together, the heel, instep and toe 22, 24, 26 form a foot that closely replicates the structure and form of an anatomical foot. FIG. 1 also shows in phantom a cosmesis 28, which is molded around prosthetic foot 10. Cosmesis 28 is preferably constructed of foamed polyethylene.

It is preferred that the x axis, about which joint 30 is designed to rotate, be positioned at approximately twenty-five to thirty percent (25–30%) of the distance from heel 22 to toe 26. In addition, it is preferred that the transition from instep 24 to toe 26 occur at approximately seventy-five percent (75%) of the distance from heel 22 to toe 26.

It is further preferred that the height, or depth, of instep 24 be approximately 4%, 6%, or 8% of the length of foot prosthesis 20 for soft, medium and firm prostheses, respectively. This allows the cross-section perpendicular to the y axis of instep 24 to be great enough to provide the necessary rigidity through the middle of the foot, while maintaining the x axis as low as possible.

Foot prosthesis 20 is preferably constructed of a molded copolymer comprising approximately 100% polypropylene. It is further preferred that the polypropylene be black, as it has been found that black polypropylene avoids both excessive creep and excessive brittleness, while providing sufficient resilience for the present application. Other materials having suitable physical properties may be substituted for these polymers without departing from the spirit of the invention.

Foot prosthesis 20 is preferably formed by molding a working piece of the copolymer around a rigid model having a desired shape. It has been found advantageous to at least partially evacuate a region adjacent to the model. This allows the surrounding atmosphere outside the working piece to apply isostatic pressure to the piece, thereby causing it to conform smoothly and completely to the form. Alternatively foot prosthesis 20 may be injection molded. For lightness, the molded underside (not shown) of raised instep 24 may include a hollow recess, as discussed in greater detail below.

Figure 4:
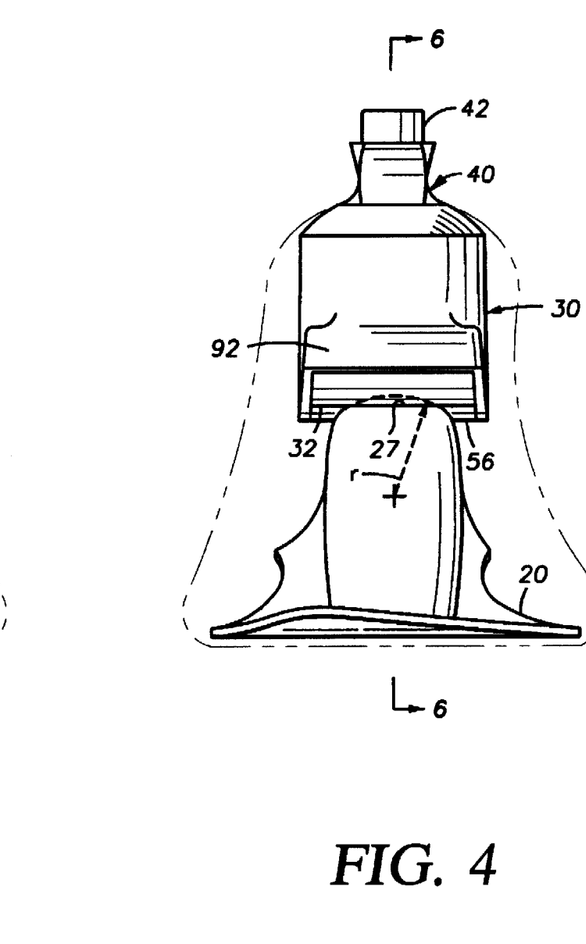
FIG. 4 is a front elevation of the prosthetic foot of FIG. 1.
Figures 5, 5A:
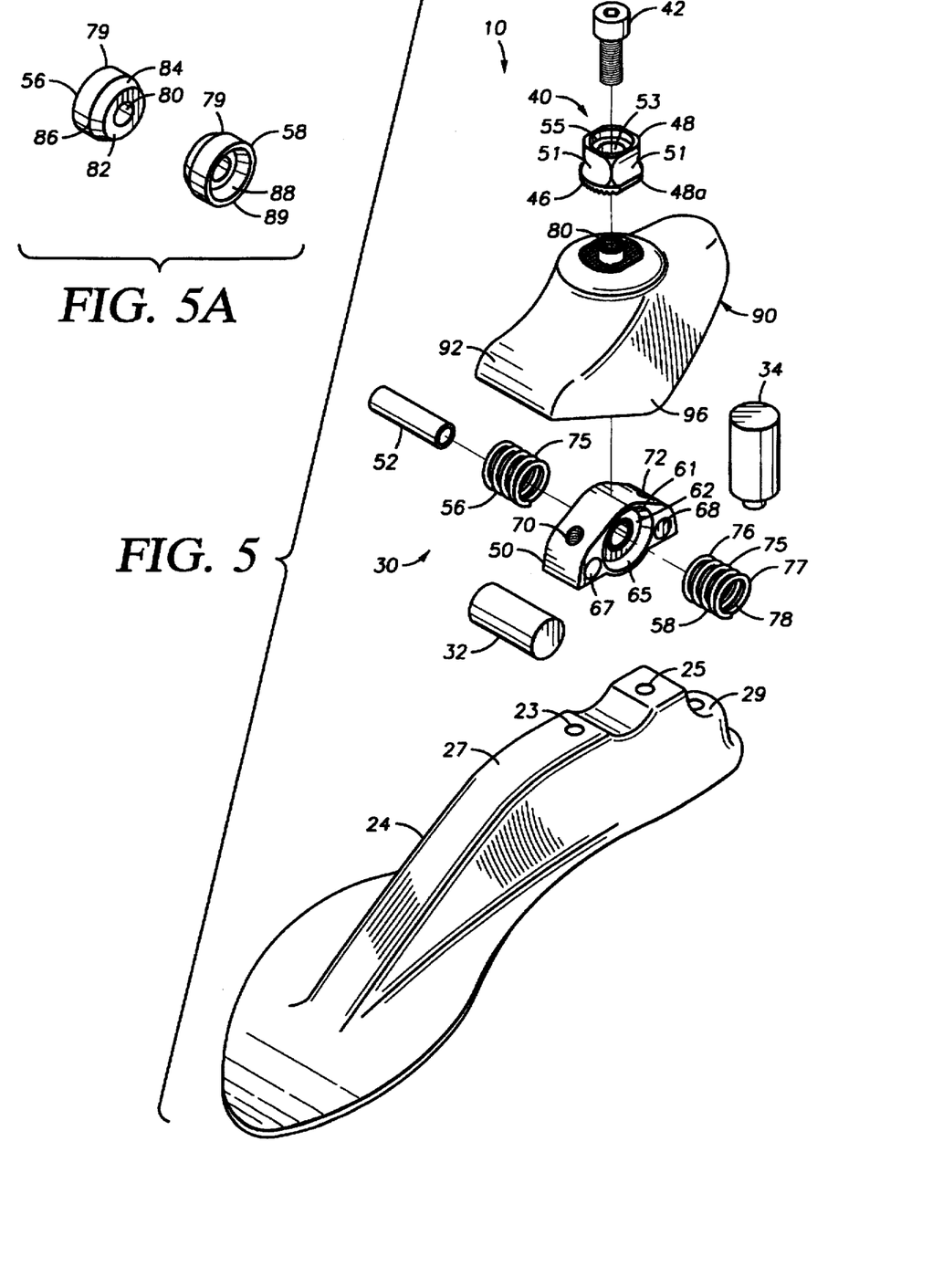
FIG. 5 is an exploded view of the prosthetic foot of FIG. 1 without the cosmesis.
FIG. 5A is an exploded view of the internal components of the ankle joint of FIG. 5.
Figure 6:
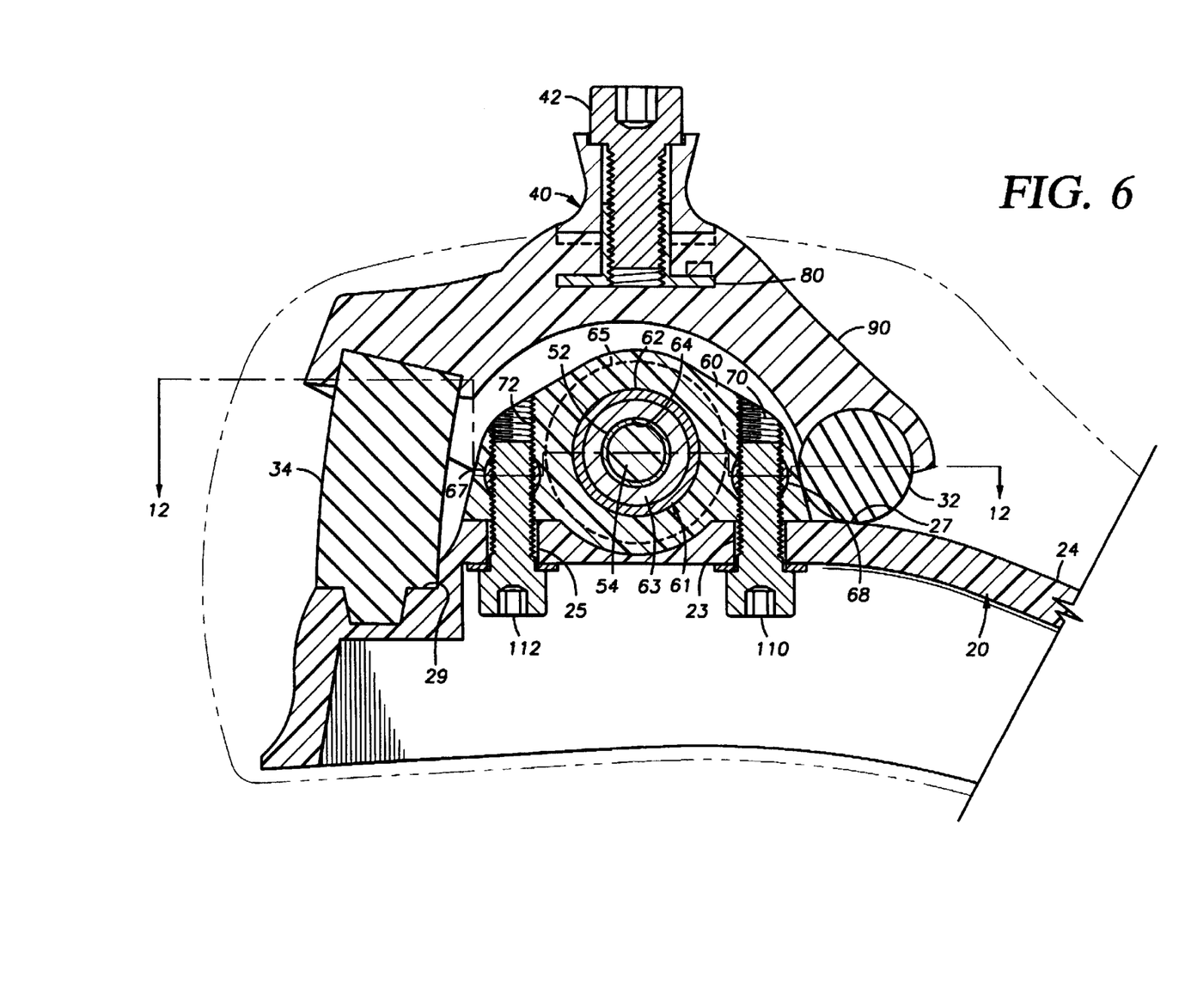
FIG. 6 is a side cross-sectional view taken along lines 6—6 of FIG. 4.

Referring briefly to FIGS. 5 and 6, instep 24 includes a forward vertical bore 23 and a rear vertical bore 25 therethrough. Instep 24 further includes a curved front contact surface 27 and a planar rear contact surface 29 on its upper, or dorsal surface. As best shown in FIG. 4, contact surface 27 has a radius of curvature r.

Multi-Axial Joint

Referring now to FIGS. 5 and 5A, the components of prosthesis 10 are shown in exploded form. As set out in greater detail in copending applications 08/134,384 and 08/040,905, ankle joint 50 can be constructed in a variety of ways. As shown in FIGS. 5 and 5A, the first, multiaxial joint embodiment is built around a swivel joint that allows rotation around any of three perpendicular axes. According to this embodiment, joint 30 comprises a body 50, a roll pin 52, a pair of compression mounts 56, 58, and a shell 90. Shell 90 includes a forward cup 92, a rear cup 94 and a pair of side portions 96. Side portions 96 extend through roll pin 52 to form an integral axle 54. Shell 90 forms axle 54 and interconnects body 50, and compression mounts 56, 58 as described in detail below.

Figure 7:
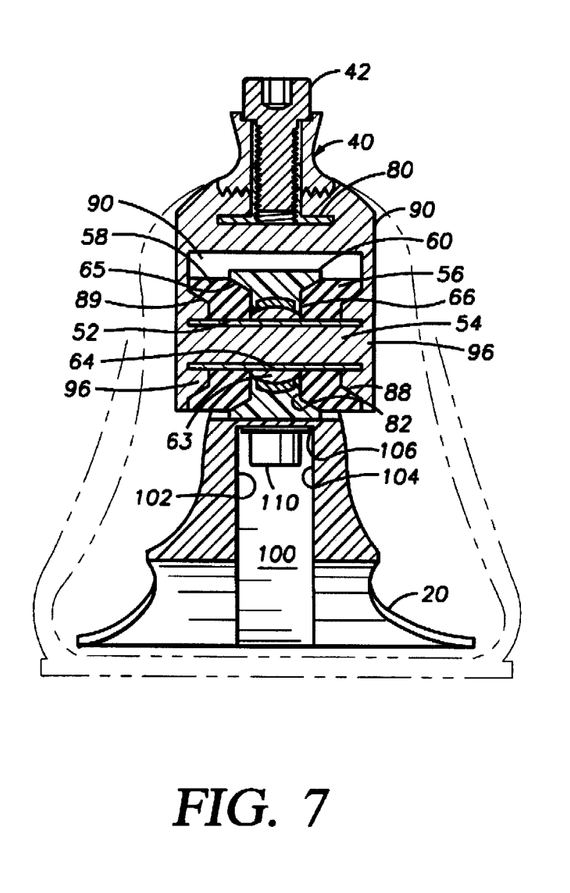
FIG. 7 is a cross-sectional view taken along lines 7—7 of FIG. 2.

As best shown in FIGS. 6 and 7, body 50 includes an oblong housing 60 in which a swivel joint 61 is transversely mounted. Swivel joint 61 includes an outer race 62 (shown in phantom). Outer race 62 supports an inner race 63. Inner race 63 is rotatable within outer race 62 and has a central bore 64 therethrough. Bore 64 is adapted to receive roll pin 52 such that axle 54 engages bore 64 in an interference fit and lies substantially on the x axis. Such swivel joints are commonly available, one being manufactured by Boston Gear, a subsidiary of Incom International, Inc. of Quincy, Mass.

Axle 54 must be capable of withstanding significant shear stresses. Therefore, it is preferable that axle 54 be constructed of epoxied unidirectional glass fiber. To construct axle 54 in this manner, roll pin 52 is driven into bore 64 with its expansion opening upwards, glass fiber is drawn through roll pin 52 and arranged with additional glass fiber in a mold to complete shell 90. When epoxy is poured into the mold and cures, axle 54 and shell 90 are formed simultaneously in one piece. Roll pin 52 acts as a bearing between axle 54 and body 50. Commercially available roll pins have been found suitable for use as pin 52.

In an alternative embodiment (not shown) axle 54 can comprise a single piece of rigid material, such as steel, which is placed through bore 64 of swivel joint 61. In this case, axle 54 is not integral with the sides 96 of shell 90, but is affixed thereto when its ends are embedded in the epoxy forming shell side portions 96.

Still referring to FIGS. 6 and 7, each side face of housing 60 includes an annular bevel 65 centered on swivel joint 61. Bevel 65 forms an annular seating face 66. Parallel to and proximate swivel joint 61 are a forward transverse support 67 and a rear transverse support 68. A pair of vertical bores 70, 72 pass through body 50, intersecting transverse supports 67 and 68, respectively. For structural purposes, it is desired that the diameter of supports 67, 68 exceed the diameter of bores 70, 72. This ensures that a potion of each support extends beyond the bore, as shown.

Referring again to FIGS. 1-6, a forward snubber 32 and a rear snubber 34 are interposed between foot prosthesis 20 and ankle joint 30 as discussed in greater detail below. Snubbers 32 and 34 comprise cylindrical resilient members and are preferably constructed of rubber, neoprene, high density urethane, or the like. A preferred material for the construction of snubbers 32, 34 is a polyurethane sold under the registered trademark Flexane® and manufactured by ITW Devcon, 30 Endicott St., Danvers, Mass. 01923.

It is further preferred that contact surface 27 of foot prosthesis 20 further be provided with a hatched or toughened surface. This prevents the formation of a seal between forward snubber 32 and surface 27. The passage of air between snubber 32 and surface 27 minimizes slippage of the snubber and prevents undesirable sounds that would otherwise be emitted as snubber 32 engages surface 27.

Single Axis Joint

In some instances it may be desired to allow rotation of the joint around only one axis, rather than all three. In these cases, a second embodiment of the joint is used. According to the second joint embodiment shown in FIGS. 8 and 8A, ankle joint 30 comprises a body 150, a liner 154, a tubular bearing 158 and a shell 90. Shell 190 includes a forward cup 192, a rear cup 194 and a pair of side portions 196. Shell 190 is connected to and surrounds body 150, liner 154 and bearing 158 by means of an integral axle 162, as described in detail below.

Figures 8, 8A:
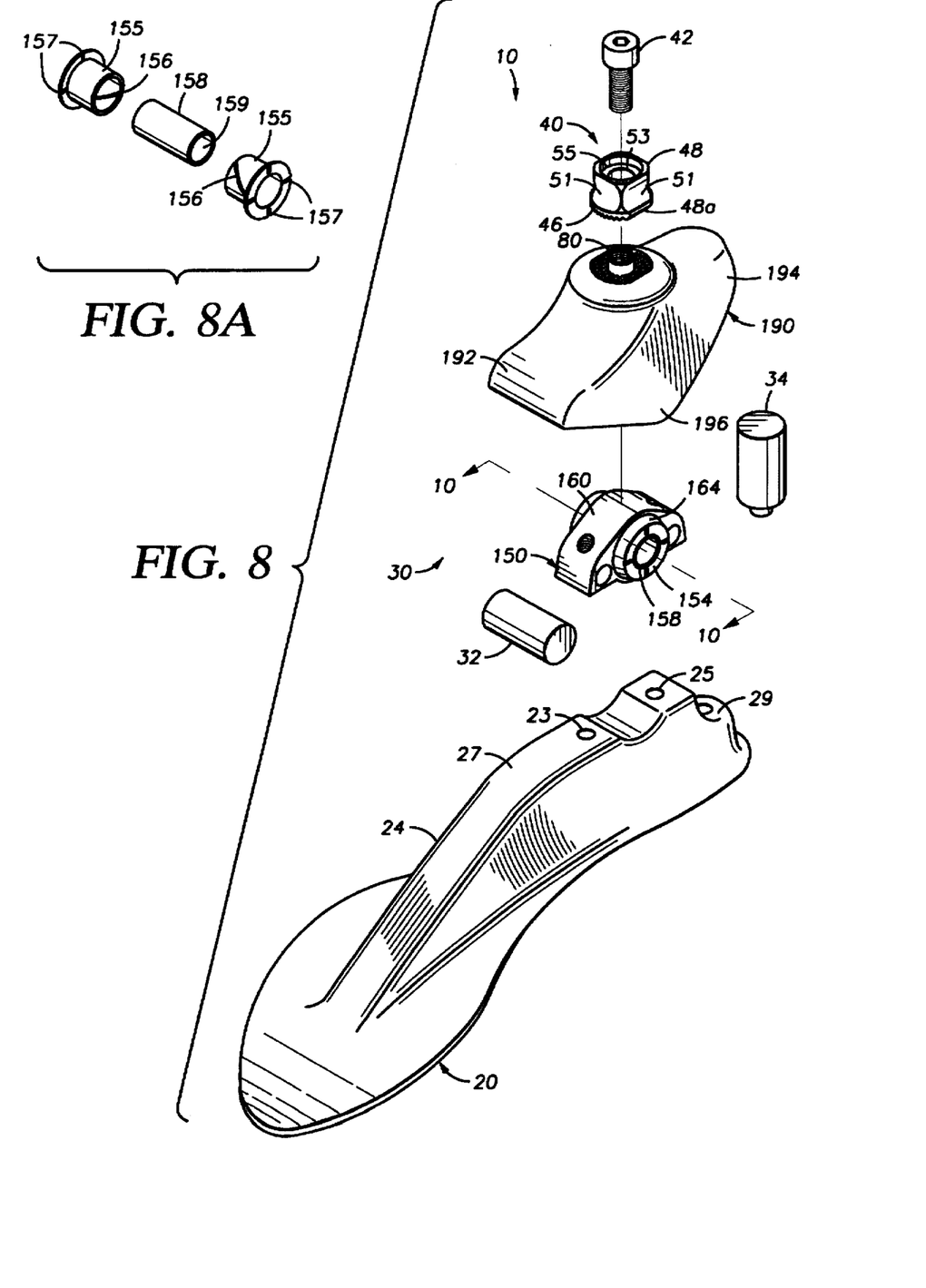
FIG. 8 is an exploded view of the prosthetic foot showing a second joint embodiment.
FIG. 8A is an exploded view of the internal components of the ankle joint of FIG. 8.
Figure 9:
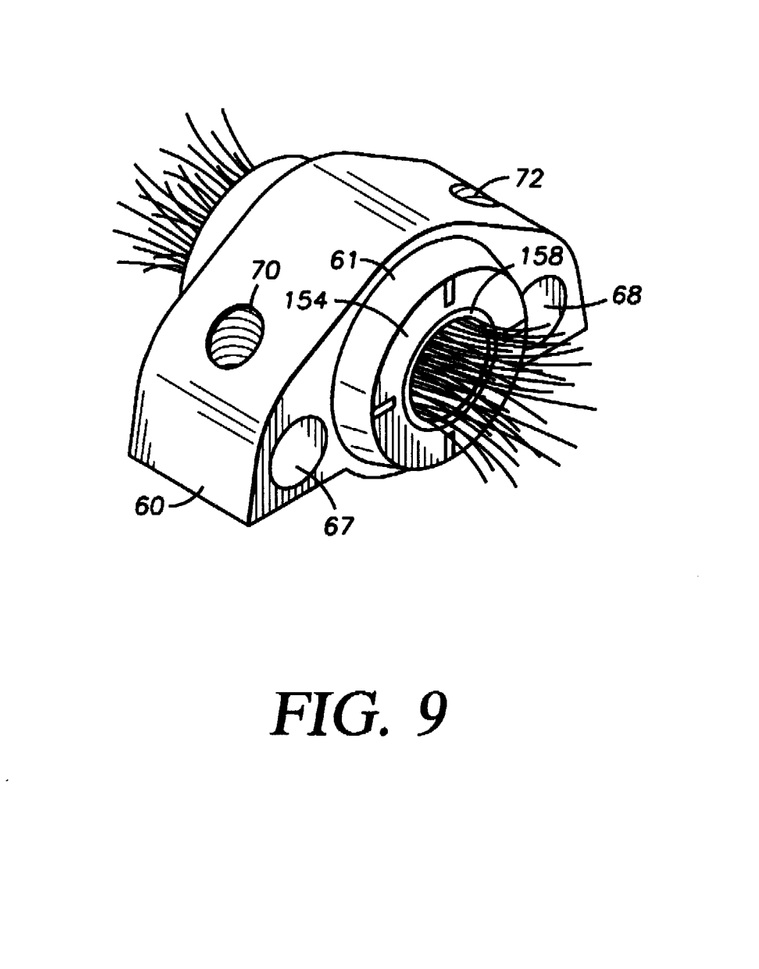
FIG. 9 is a perspective view of the second joint embodiment shown in FIG. 8, at an intermediate manufacturing step.
Figure 10:
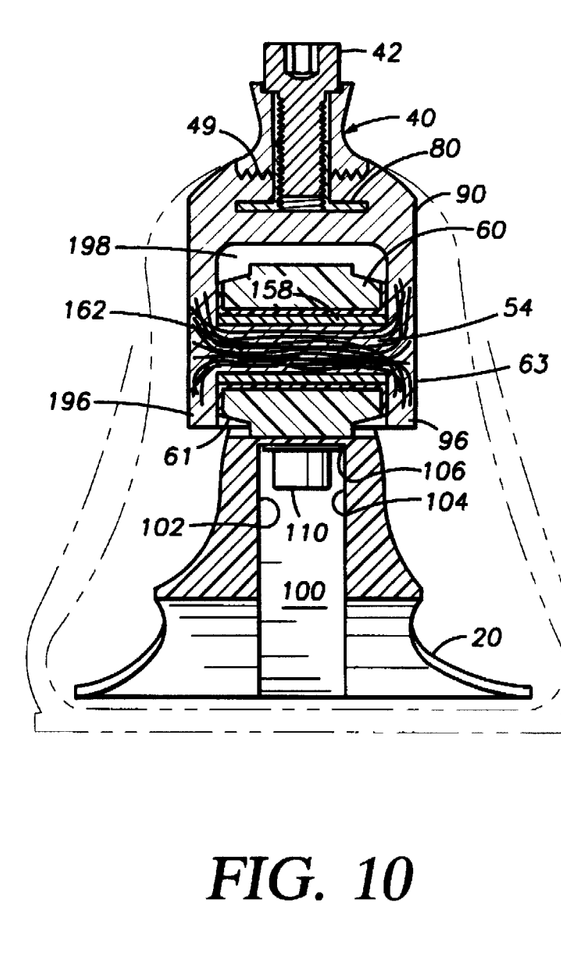
FIG. 10 is a cross-sectional view taken along lines 10—10 of FIG. 9.

Referring to FIGS. 8-10, body 150 includes an oblong housing 160 in which liner 154 is transversely mounted, i.e., parallel to the x axis. Each side of housing 160 includes raised annular bevel 164 centered on the x axis. Bevel 164 contributes to the stability of the joint by allowing axle 162 to be slightly longer than the width of body 160.

As best seen in FIG. 8A liner 154 preferably comprises a pair of identical flanged tubes 155. Tubes 155 are positioned within body 150, so that their unflanged ends abut to form liner 154, which spans the width of housing 160 at bevel 164. According to the preferred embodiment, each tube 155 includes an expansion opening 156 along its entire length and a plurality of radial slots 157 at the outer edge of the flange. Tubes 155 are preferably constructed from nylon or other suitable polymer, and may be purchased under the trademark Nyliner, sold by Seastrom Manufacturing Company, Inc., 701 Sonora Ave., Glendale, Calif. 91201-2495.

Liner 154 is sized to receive bearing 158 coaxially, with the inner surface of tubes 155 adjacent the outer surface of bearing 158, such that bearing 158 also lies on the x axis within body 150. Bearing 158 has an inner surface 159 and is preferably any suitable brass tubing. For example, a suitable tubing has an outside diameter of 0.50 inches and an inside diameter of 0.45, such as is commonly commercially available. Other materials may be used for liner 154 and bearing 158, so long as they are capable of providing a bearing surface at the liner/bearing interface and are suitable for use in the present application.

Referring particularly to FIG. 10, it will be seen that side portions 196 of shell 90 extend inwardly through bearing 158 to form integral axle 162 extending through bearing 158. Forward and rear cups 192, 194 (shown in FIG. 8) and side portions 196 of shell 90 enclose body 150, with side portions 196 being integral with axle 162. Between shell 90 and the top of body 150 is a void 198.

As discussed above with respect to the multi-axial joint, the single axis joint is provided with a forward transverse support and a rear transverse support passing through body 150 parallel to the x axis. A pair of threaded vertical bores also pass through body 150. Similarly, forward and rear snubbers 32, 34 are positioned to limit relative motion of the joint and foot prosthesis.

Modified (Syme) Foot

As mentioned above, patients who have undergone ankle disarticulation surgery retain some of the ankle bones adjacent their lower legs, but do not have any flexibility at that joint. Because of the nature of the ankle disarticulation patient's lower limb, conventional connectors such as the Otto Both connector are not suitable for this application, as they take up too much of the clearance between the floor and the lower end of the leg.

In accordance with the objectives of the present invention, the prosthesis can be modified so as to allow it to affixed to the lower limb of an ankle disarticulation patient without an Otto Boch or similar connector. According to this second preferred embodiment, both the foot and joint of the present prosthesis are modified. The present invention allows the patient to re-gain a flexible ankle joint, whereas previous foot prostheses provided for ankle disarticulation patients comprise a foot only and do not provide a flexible ankle joint.

Figure 11:
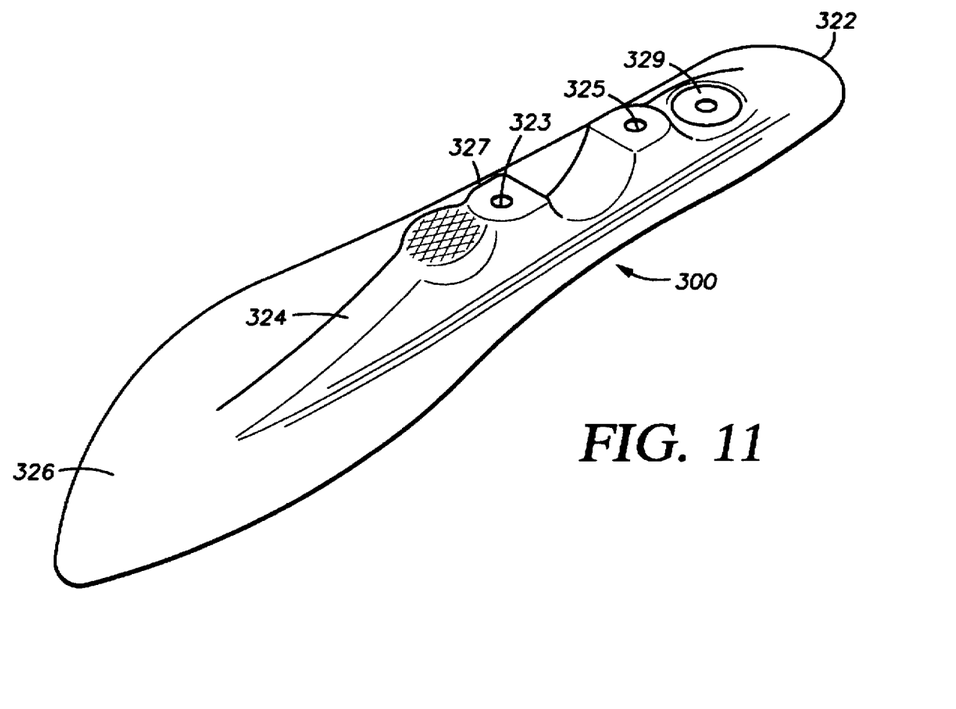
FIG. 11 is a perspective view of a second embodiment of the foot prosthesis of the present invention.
Figure 12:
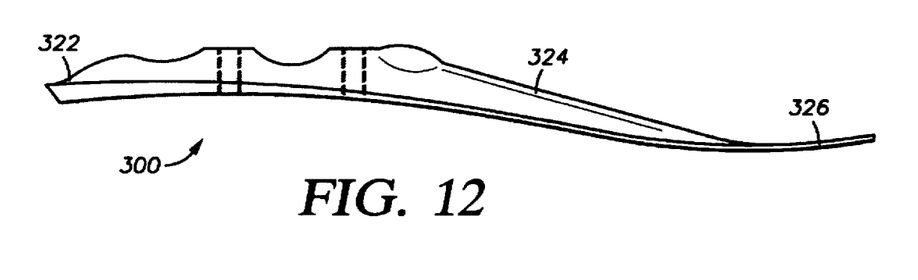
FIG. 12 is a side elevation of the foot prosthesis shown in FIG. 11.

Referring now to FIGS. 11 and 12, the modified foot prosthesis 300 comprises a heel 322, a raised instep 324, and a substantially flat toe potion 326. As with foot prosthesis 20 above, instep 324 includes a groove 310 adjacent its plantar surface, and a curved front contact surface 327 and a rear contact surface 329 on its upper, or dorsal side. Rear contact surface 329 surface is significantly reduced in height, so as to be approximately half or less than half of the height of the forward contact surface 327. The saddle portion of the instep between bores 323 and 325 is also lowered and inclined somewhat toward the heel. In this manner a joint that is affixed to foot prosthesis 300 will have an axis of rotation that is approximately 0.25 inches lower than a joint affixed to the unmodified foot described above. For example, the axis of a joint affixed to a firm modified foot prosthesis 300 (in which the height of the instep is approximately 8% of the length of the foot) is preferably less than about 1.5 inches above the floor and is more preferably less than about 1.25 inches above the floor. Incorporation of the Syme foot into prosthesis 10 is discussed in greater detail below.

Modified (Syme) Joint

Figure 13:
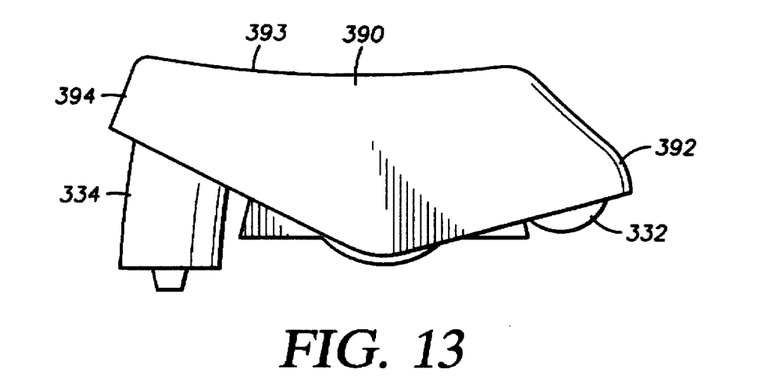
FIG. 13 is a side elevation of a third joint embodiment.

Referring now to FIG. 13, when it is desired to provide a prosthesis to a Syme patient, the shell 90 of joint 30 is modified in a third embodiment by reducing the depth of rear cup 94 and eliminating the upper portion of shell 90 that would otherwise support a connector. Rear snubber 34 is also shortened. These modifications, together with the modifications of the foot 300 described above, can be combined with either the multi-axial joint or the single axis ankle joint to allow the prosthesis to fit between foot 300 and the lower end of a Syme patient's leg.

For convenience and clarity, the balance of the discussion of the present foot will be in terms of the multi-axial joint. It will be understood by those skilled in the art, however, that the single axis joint can be substituted for the multi-axial joint and used in combination with any embodiment of the other parts of this invention.

Attachment of Joint to Foot

A functional prosthesis is formed by attaching a joint to the foot prosthesis, such that when a lower leg, either prosthetic or natural, is connected to the joint, the joint will allow relative movement of the leg and foot. Attachment of the joint to the foot is preferably accomplished by means of a pair of bolts, as next described.

Referring now to FIGS. 6 and 7, instep 24 of foot prosthesis 20 includes a lower recess 100. Preferably, recess 100 comprises a longitudinal groove in instep 24 having side walls 102, 104 and an inner wall 106. As shown in FIGS. 5 and 6, vertical bores 23, 25 are located in inner wall 106.

Ankle joint 30 is preferably attached to foot prosthesis 20 by means of a pair of bolts 110, 112. Bolts 110, 112 pass through bores 23, 25, respectively and engage bores 70, 72, respectively, in body 50. It will be understood that bolts 110, 112 could be replaced with a single bolt, or other suitable attachment means. It is believed advantageous, however, to use at least two such attachment means, as it reduces fatigue in the attachment, even if the attachment(s) develop slack.

Before foot prosthesis 20 is connected to body 50, snubber 32 is positioned transversely within the forward cup 92 of shell 90 so that it rests on front contact surface 27, as best illustrated in FIG. 8. Snubber 32 is sized so that its diameter is approximately equal to the distance between contact surface 27 of instep 24 and the underside of forward cup 92 of shell 90. Because contact surface 27 is curved from side to side, only the center portion of forward snubber 32 contacts surface 27 in the normal, unflexed position. Rear snubber 34 is positioned vertically within the rear cup 94 of shell 90 so that it rests on contact surface 29. Snubber 34 is sized so that its length is approximately equal to the distance between planar surface 29 of instep 24 and the underside of rear cup 94 of shell 90.

The modified (Syme) joint can be affixed to the modified (Syme) foot in the same manner.

Connection of Joint to Leg

Standard Connection

As disclosed in the copending applications mentioned above, connector 40 may be affixed to shell 90 by means of a T-nut 80 and a bolt 42. Connector 40. comprises an annular flange 48a adjacent one end of a coaxial four-sided body 48. The lower face of flange 48a preferably includes a plurality of longitudinal grooves 46 that run from the front to the back of the flange. Body 48 includes four curved faces 51 and a central bore 53 therethrough. Surrounding bore 53 is an annular recess 55, which is adapted to receive the head of bolt 42. T-nut 80 comprises a body 82 having a threaded bore 84 and a terminal flange 86, which supports four locking tabs (not shown). Preferably, T-nut 80, connector 40 and bolt 42 are made of metal and most preferably of steel. It has been found that 316 alloy steel is well suited to the present application.

Connector 40 is preferably the male component of a standard adjustable connection formerly manufactured by the Otto Boch Corp. of West Germany and now widely available. Because of its strength and adjustability, this type of connection is presently used for virtually every non-flexible prosthetic connection. This type of connection utilizes four threaded pins to engage four concave faces, allowing the connector to engage a leg prosthesis and to lock in almost any desired relationship.

Modified (Syme) Connection

Figure 14:
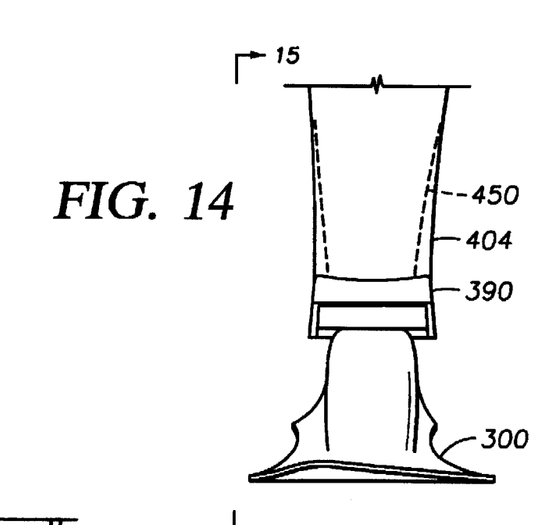
FIG. 14 is a front elevation showing the third joint embodiment of FIG. 13 connected to the second foot prosthesis and a leg cuff.
Figure 15:
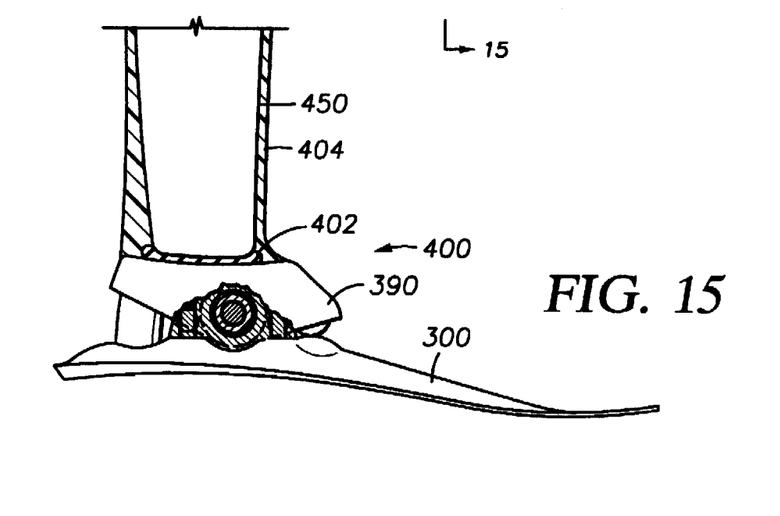
FIG. 15 is a cross-sectional view taken along lines 15—15 of FIG. 14.

When it is desired to fit a Syme patient with the present articulated prosthetic foot, the connector 40 is omitted and a flat upper surface 393 is formed on shell 390 as shown in FIG. 13. Attachment of the modified joint to the wearer's leg is as follows:

First, the lower leg of the amputee is fitted with a close-fitting removable rigid cuff that includes a conventional female connector adjacent its lower end. A prosthesis having a conventional male connector is then connected to the connector on the sleeve and adjusted according to conventional methods, thereby defining a customized and comfortable relationship between the leg and prosthesis. As is known in the art, the Otto Boch connector can be tightened and fixed in the customized relationship. The sleeve is then removed from the amputee's leg while preserving the customized leg/prosthesis relationship by means of the connector. At this point, the customized relationship can be measured using conventional means, and recreated between a modified prosthesis 400 and a second, permanent cuff 450, as shown in FIGS. 14 and 15. Because the modified prosthesis and second sleeve lack the Otto Boch connector and are therefore able to be joined in a much closer relationship, the entire jointed prosthesis can fit into the reduced clearance between the lower end of the amputee's limb and the floor.

Since a connector 40 is not used, the shell 390 of the joint is permanently glued to the end of the second cuff in the previously determined customized relationship using a layer of adhesive 402. Once the connection has been made in this manner, it is preferred to provide an outer layer 404 of fiberglass and epoxy that surrounds and strengthens the connection between the joint and the sleeve. In this manner, the amputee is provided with a an ankle-jointed prosthetic foot that is affixed to a removable cuff. When the cuff is worn over the lower limb, the prosthetic ankle and foot complement and function similarly to the amputee's remaining foot.

The present invention can be manufactured in left and right configurations and can be used to replace both feet of a single patient, if necessary.

Sizing the Joint

It has been found advantageous to provide ankle joint 30 in a plurality of sizes. Specifically, it has been found that three sizes are adequate to support the normal range of necessary prosthesis sizes. For example, the size of axle 62 varies according to the desired prosthesis size; the 0.5 inch brass tubing disclosed above is suitable for a medium prosthesis.

Operation

Figure 16:
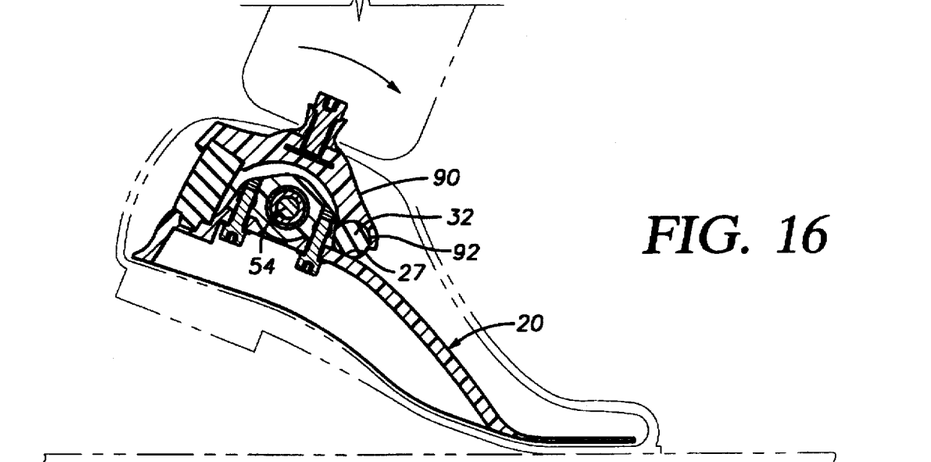
FIGS. 16–18 are sequential side elevational views of the foot of FIG. 1 showing motion of the foot and attached ankle joint through a step.

Referring now to FIG. 16, during dorsiflexion, the leg is inclined toward the front of the foot. Dorsiflexion occurs during the "push-off" phase of a normal step, or during uphill walking. In the prosthesis of the present invention, dorsiflexion causes a clockwise (as shown) moment about the x axis to be applied to shell 190. Because shell 190 is integral with axle 162, which is in turn bonded to beating 158, bearing 158 rotates within liner 154 as shell 190 pivots. Pivoting of shell 190 causes front snubber 32 to be compressed between front contact surface 27 and forward cup 192. As the degree of flexion increases, snubber 32 deforms to fully contact the curved contact surface 27. Because snubber 32 is resilient and is substantially confined within forward cup 192, it resists compression and biases foot prosthesis 20 away from forward cup 912. During normal use, a maximum dorsiflexion about axle 62 of approximately 10 to 15 degrees will occur.

For a given prosthesis size, the degree of dorsiflexion that can occur depends in part on the durometer, or hardness, of forward snubber 32. A desired durometer can be selected by modifying the composition of the snubber material. Methods for altering the durometer of a material, and of polymers in general are well known. If, as discussed above, Flexane® is used, an additive marketed under the trademark Flex-Add™ and also manufactured by Devcon, may be used to produce a softer polymer.

The radius of curvature r of contact surface 27 also affects the resistance of joint 30 to dorsiflexion. The smaller the radius of curvature r of contact surface 27, the smaller the area is of surface 27 that contacts snubber 32. With a smaller area, greater pressure will be applied by a given force, causing greater deformation. A surface 27 having a smaller radius of curvature will distort snubber 32 to a greater degree and allow more degrees of dorsiflexion with the same force. Thus, the same effect can be achieved by providing either a softer snubber or a smaller radius of curvature for contact surface 27.

The height of instep 24 can also affect the dorsal flexibility of the prosthetic foot. Because the flexibility of an object depends on its cross-section in the direction of flexure, raising the height of instep 24 produces a stiffer foot. Likewise, a more flexible foot can be produced by decreasing the height of instep 24. Because foot prosthesis 20 is made of polypropylene in a preferred embodiment, it is capable of some flexure without breaking.

Figure 17:
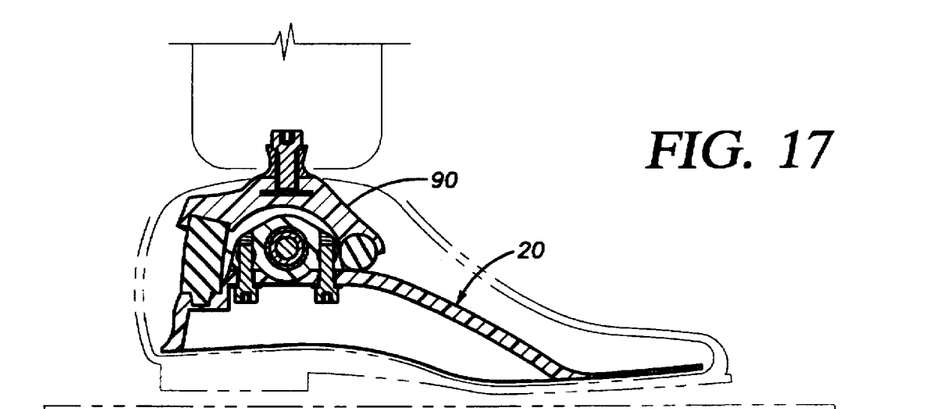

In contrast to instep 24, toe portion 26 of foot prosthesis 20 has a small cross-sectional area, and therefore flexes relatively easily. Hence, as the wearer's body mass moves forward over the foot and begins to straighten the ankle, the energy stored in front snubber 32 is transferred into flexure of toe portion 26. When the toe of prosthesis 10 leaves the ground, moment is removed from the joint and prosthesis 10 returns to its unflexed position as the leg swings forward, as shown in FIG. 17. It is preferred that joint 30 store only a minimum amount energy, that amount being the amount necessary to return the prosthesis to its unflexed position. It is preferred that excess energy be dissipated within the resilient components of joint 30, so as to avoid an excessively bouncy step. The degree to which energy is dissipated, rather than being released, can be controlled by modifying the composition and structure of the resilient components.

Figure 18:
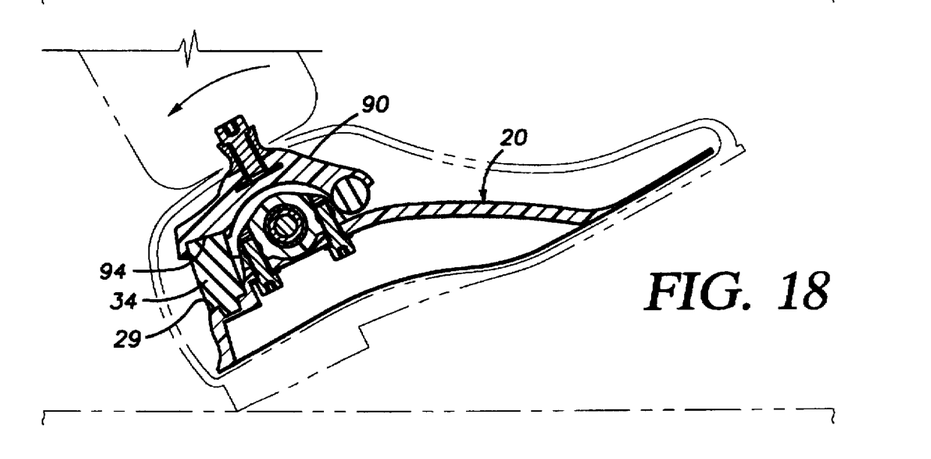

Referring now to FIG. 18, when the heel of prosthesis 10 is placed on the ground, a counter-clockwise moment is applied to the joint, resulting in planiflexion. As in dorsiflexion, shell 190 pivots, this time in a counter-clockwise direction about the x axis, causing bearing 158 to rotate liner 154. Rear snubber 34 is compressed between rear contact surface 29 of instep 24 and rear cup 194 of shell 190, and biases prosthesis 10 to return to an unflexed position. In addition, rear snubber 34 provides more shock-absorbing capability. Because it is oriented so that the compressive forces are applied along its longitudinal axis, it is capable of compression through a greater distance than the transversely mounted front snubber 32. During normal use, a maximum planiflexion about axle 62 of approximately 10 to 30 degrees will occur. Once the foot is planted, as the wearer moves forward the moment is removed and prosthesis 10 returns to an unflexed position before commencing the next push-off.

Figure 19:
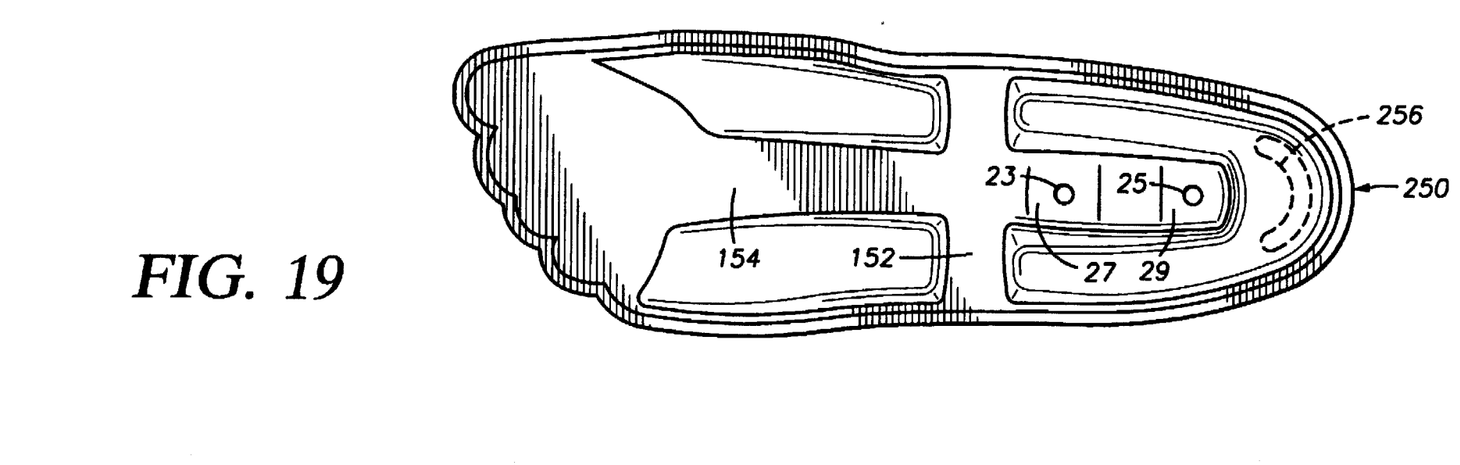
FIGS. 19 and 20 are plan views of two sections of a cosmesis according to the present invention.

Other aspects of the present invention are the internal construction of cosmesis 28 itself and the inclusion of a protective resilient member between heel 22 and the heel portion of the cosmesis, as shown in FIG. 19. It has been found that the configuration of the "hard" portions of the present prosthesis, i.e., the foot and ankle joint, lend themselves particularly well to a cosmesis adapted to provide naturalistic cushioning as well as a semi-rigid instep suitable for supporting the laced upper of a shoe.

Figure 20:
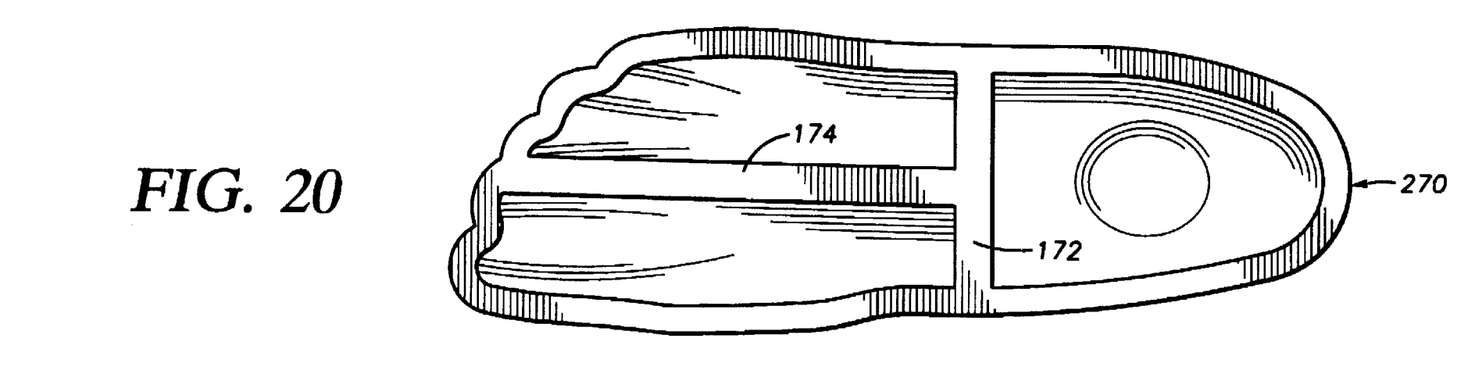

Specifically, and as shown in FIG. 19–20, the present cosmesis comprises a pair of essentially hollow sections 250, 270, each with a wall thickness of about 0.25 inches. Plantar section 250 corresponds to the lower, or sole, portion of the foot and houses the hardware of the prosthesis. Section 250 is preferably molded around a foot prosthesis 20, leaving the upper surfaces of foot prosthesis 20 that support joint 30, namely contact surfaces 27, 29 and the concave mounting surface therebetween, exposed. Alternatively, foot prosthesis 20 can be placed into section 250 after it has been formed and affixed by means of adhesive. In either instance, it is preferred to include an insert 256 formed of a resilient material between heel 22 and the cosmesis. Insert 256 preferably comprises a tough and rubbery material, such as silicone. Insert 256 spreads the load applied by the heel of the foot prosthesis, and decreases the wear on the cosmesis.

Dorsal section 270 corresponds to the upper contours of the foot and may be designed to include simulations of such naturalistic features as toes and musculature on its outer surface. Fixed within each cosmesis section 250, 270 are a transverse support 152, 172 and a sagittal support 154, 174. Longitudinal support 154 in lower section 250 coincides with and encases instep 24 of foot prosthesis 20. Supports 152, 172 are transversely positioned just forward of front contact surface 27 and create a firmly supported instep that is suitable for receiving a lace-up shoe. Supports 152, 172 are aligned when the prosthesis is assembled. Sagittal supports 154, 174 extend perpendicularly forward from transverse supports 152, 172, and are also aligned when the prosthesis is assembled. Supports 152, 172 and 154, 174 are preferably formed from the same foamed material as cosmesis 28. While the supports can be molded into their respective sections 250, 270, it is easier to construct the supports separately and then insert and affix them into sections 250, 270. As stated above, together supports 152, 172 and 154, 174 improve the operation and feel of the prosthesis.

An advantage of the joint of the present invention lies in the fact that it closely simulates the motion of an anatomical foot about the x axis while providing a lightweight, stable foot that is easily adapted to normal use.

What is claimed is:

1. A lightweight foot prosthesis formed from a single piece of material, comprising:
   a heel;
   a relatively narrow, substantially rigid, raised instep having a lower surface and a groove adjacent said lower surface and having forward and rear contact surfaces, said contact surfaces defining a saddle-shaped surface therebetween; and
   a substantially flat toe extending forward from said instep.

2. The foot prosthesis according to claim 1 wherein said foot comprises a single piece of molded polymer.

3. The foot prosthesis according to claim 1, further including a joint affixed to said saddle-shaped surface, said joint being capable of rotation about a substantially horizontal axis.

4. The foot prosthesis according to claim 3 wherein said substantially horizontal axis is positioned at approximately twenty-five to thirty percent (25–30%) of the distance from said heel to said toe.

5. The foot prosthesis according to claim 3 wherein said joint comprises a shell, a housing, a swivel joint that is capable of rotation about three perpendicular axes, and an axle, said swivel joint being mounted horizontally in said housing and said axle passing through said swivel joint and being connected at its ends to said shell.

6. The foot prosthesis according to claim 5 wherein said axle is integral with said shell.

7. The foot prosthesis according to claim 3 wherein said joint comprises a housing, a shell, a bearing horizontally mounted in said housing and an axle passing through said bearing.

8. The foot prosthesis according to claim 7 wherein said axle is integral with said shell.

9. The foot prosthesis according to claim 1 wherein the transition from said instep to said toe is positioned at approximately seventy-five percent (75%) of the distance from said heel to said toe.

10. The foot prosthesis according to claim 1 wherein the height of said saddle-shaped surface is approximately 4–8 percent of the length of said foot prosthesis.

11. The foot prosthesis of claim 1, further including a cosmesis including dorsal and plantar sections, each section being sagittally and transversely internally supported.

12. The foot prosthesis of claim 11 wherein said plantar cosmesis section is adapted to support said foot and includes a rubbery insert adjacent said heel.

13. The foot prosthesis of claim 11 wherein said dorsal cosmesis section is adapted to receive a joint device.

14. A prosthesis for use by an ankle disarticulation patient, comprising:
   a foot comprising a heel, a substantially flat toe, and a relatively narrow, substantially rigid, raised instep having a lower surface and a groove adjacent said lower surface and having forward and rear contact surfaces, said rear contact surface having a height that is less than the height of said forward contact surface, said contact surfaces defining a saddle-shaped surface therebetween, said toe extending forward from said instep; and
   a joint seated in said saddle-shaped surface and affixed to said foot, said joint providing a substantially horizontal axis of rotation and an upper connecting surface;
   wherein the total height of said joint and foot is less than the clearance between the floor and a disarticulated ankle.

15. The prosthesis according to claim 14, further including a cuff affixed to said upper connecting surface.

16. The prosthesis according to claim 15 wherein said cuff is affixed to said upper connecting surface by means of an adhesive and the connection therebetween is reinforced with fiberglass.

17. The prosthesis according to claim 14 wherein said axis of rotation is less than about 1.5 inches above a plantar surface of the prosthesis.

18. The prosthesis according to claim 14 wherein said rear contact surface is less than half the height of forward contact surface.

* * * * *